(12) United States Patent
Lee

(10) Patent No.: US 9,408,773 B2
(45) Date of Patent: *Aug. 9, 2016

(54) COMPRESSION VEST FOR PATIENTS UNDERGOING HEMODIALYSIS AND IN CRITICAL CARE

(71) Applicant: Global Monitors, Inc., Rancho Santa Fe, CA (US)

(72) Inventor: Jen-shih Lee, Rancho Santa Fe, CA (US)

(73) Assignee: GLOBAL MONITORS, INC., Rancho Santa Fe, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/265,009

(22) Filed: Apr. 29, 2014

(65) Prior Publication Data

US 2014/0236058 A1    Aug. 21, 2014

Related U.S. Application Data

(63) Continuation-in-part of application No. 12/977,574, filed on Dec. 23, 2010, now Pat. No. 9,155,541, which is a continuation-in-part of application No. 12/062,944, filed on Apr. 4, 2008, now Pat. No. 7,879,069.

(60) Provisional application No. 61/000,436, filed on Oct. 26, 2007.

(51) Int. Cl.
*A61H 11/00* (2006.01)
*A61B 17/135* (2006.01)
(Continued)

(52) U.S. Cl.
CPC ............ *A61H 11/00* (2013.01); *A61B 17/1355* (2013.01); *A61H 9/0078* (2013.01); *A61H 2201/0173* (2013.01); *A61H 2201/0184* (2013.01); *A61H 2201/165* (2013.01); *A61H 2201/5007* (2013.01); *A61H 2201/5035* (2013.01); *A61H 2201/5043* (2013.01);
(Continued)

(58) Field of Classification Search
CPC ........... A61H 9/0078; A61H 2205/083; A61H 2201/165; A61H 2201/5071; A61H 2201/0173; A61H 2201/5007; A61H 2201/5035; A61H 2201/5043; A61H 2201/0184; A61H 11/00; A61M 1/342; A61B 17/1355

See application file for complete search history.

(56) References Cited

U.S. PATENT DOCUMENTS 2,588,192 A    3/1952  Akerman et al.
3,683,655 A    8/1972  White et al.
(Continued)

OTHER PUBLICATIONS

Smit et al., article "Use of lower abdominal compression to combat orthostatic hypotension" in Clinical Autonomic Research, Jun. 2004; 14(3):167-75).*

(Continued)

*Primary Examiner* — Quang D Thanh
(74) *Attorney, Agent, or Firm* — Weitzman Law Offices, LLC

(57) ABSTRACT

A method of inhibiting hypotensive symptoms in a patient undergoing treatment or a procedure involves elastically constraining the internal organs within the abdomen of the patient while applying non-pulsating, compressive pressure to the internal organs within the abdomen of the patient. The method may also involve one or more of infusing fluid, applying the compressive pressure using compression device, or applying the compressive pressure based upon bio-indicator measurement parameters.

5 Claims, 12 Drawing Sheets

(51) Int. Cl.
*A61H 9/00* (2006.01)
*A61M 1/34* (2006.01)

(52) U.S. Cl.
CPC ... *A61H2201/5071* (2013.01); *A61H 2205/083* (2013.01); *A61M 1/342* (2013.01)

(56) References Cited

U.S. PATENT DOCUMENTS

| | | | |
|---|---|---|---|
| 3,920,008 A | 11/1975 | Lehman | |
| 3,933,150 A * | 1/1976 | Kaplan | A61F 5/3776 601/151 |
| 4,135,503 A | 1/1979 | Romano | |
| 4,211,218 A | 7/1980 | Kendrick | |
| 4,455,685 A | 6/1984 | Steffler et al. | |
| 4,534,338 A | 8/1985 | Crosbie et al. | |
| 4,718,891 A | 1/1988 | Lipps | |
| 4,840,167 A | 6/1989 | Olsson et al. | |
| 4,925,133 A | 5/1990 | Wurst et al. | |
| 4,926,873 A | 5/1990 | Frankenreiter | |
| 4,928,674 A | 5/1990 | Halperin et al. | |
| 4,938,208 A | 7/1990 | Dye | |
| 5,222,478 A | 6/1993 | Scarberry et al. | |
| 5,346,472 A * | 9/1994 | Keshaviah | A61M 1/1605 604/28 |
| 5,490,820 A | 2/1996 | Schock et al. | |
| 5,569,170 A | 10/1996 | Hansen | |
| 5,628,721 A | 5/1997 | Arnold et al. | |
| 5,853,396 A | 12/1998 | Bennes et al. | |
| 6,036,662 A | 3/2000 | Van Brunt et al. | |
| 6,114,303 A | 9/2000 | Blue et al. | |
| 6,485,427 B1 | 11/2002 | Lee et al. | |
| 6,615,077 B1 | 9/2003 | Zhu et al. | |
| 6,757,916 B2 | 7/2004 | Mah et al. | |
| 7,104,967 B2 | 9/2006 | Rothman et al. | |
| 7,220,229 B2 | 5/2007 | Lee et al. | |
| 7,244,225 B2 | 7/2007 | Loeb et al. | |
| 7,252,646 B2 | 8/2007 | Bolam et al. | |
| 7,537,575 B2 | 5/2009 | Hansen et al. | |
| 7,879,069 B2 * | 2/2011 | Lee | A61H 9/0078 601/151 |
| 9,155,541 B2 * | 10/2015 | Lee | A61B 17/1355 |
| 2005/0165334 A1 | 7/2005 | Lurie | |
| 2008/0255482 A1 | 10/2008 | Lurie | |

OTHER PUBLICATIONS

Maggiore et al., Thermal balance and dialysis hypotension, Int. J. Artif. Organs, vol. 18(9), pp. 518-525 (1995).

Bickell et al., Randomized Trial of Pneumatic Antishock Garments in the Prehospital Management of Penetrating Abdominal Injuries, Annals of Emergency Medicine, vol. 16(6) pp. 653-58 (Jun. 1987).

Guyton, Textbook of Medical Physiology, pp. 325-27 (W.B. Sanders Co. 4th ed. 1971).

Zhu et al., Extracellular fluid redistribution during hemodialysis; bioimpedence measurement and model; Physiol. Meas. 29 (2009) pp. S491-S501.

LaForte et al., Blood volume redistribution from a passive elastic permeable microcirculation due to hypovolemia, Am. J. Physiol. 266 (Heart Circ. Phsiol. 35) pp. H2268-H2278 (1994).

Zhu et al., Methods and reproducibility of measurement of resistivity in the calf using regional bioimpedance analysis, Blood Purif., vol. 21, pp. 131-136 (2003).

Smit et al., article "Use of lower abdominal compression to combat orthostatic hypotension" in Clinical Autonomic Research, Jun. 2004; 14(3):167-75.

PCT International Search Report for Int'l Appln No. PCT/US08/76456, dated Nov. 28, 2008 (issued in PCT application corresponding to grandparent application No. 12/062,944).

PCT Written Opinion for Int'l Appln No. PCT/US08/76456, dated Nov. 12, 2008 (issued in PCT application corresponding to grandparent application No. 12/062,944).

Denq et al., Efficacy of compression of different capacitance beds in teh amelioration of orthostatic hypotension, Clinical Autonomic Research 7, 321-326 (1997).

Lee, 1998 Distinguished Lecture: Biomechancs of the Microcirculation, An Integrative and Therapeutic Perspective, Annals of Biomedical Engineering, vol. 28, pp. 1-13 (2000).

Tanaka et al., Treatment of orthostatic intolerance with inflatable abdominal band, The Lancet, vol. 349, p. 175 (1997).

Yamamoto et al., Treatment of post-dialytic orthostatic hypotension with an inflatable abdominal band in hemodialysis patents, Kidney International (2006) 70, pp. 1793-1800.

* cited by examiner

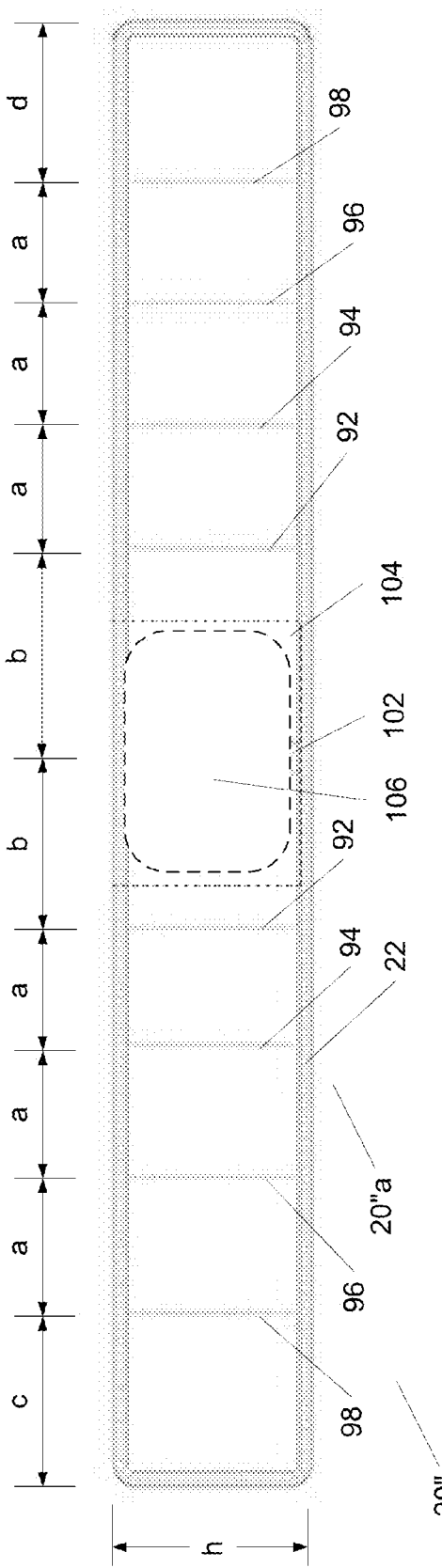
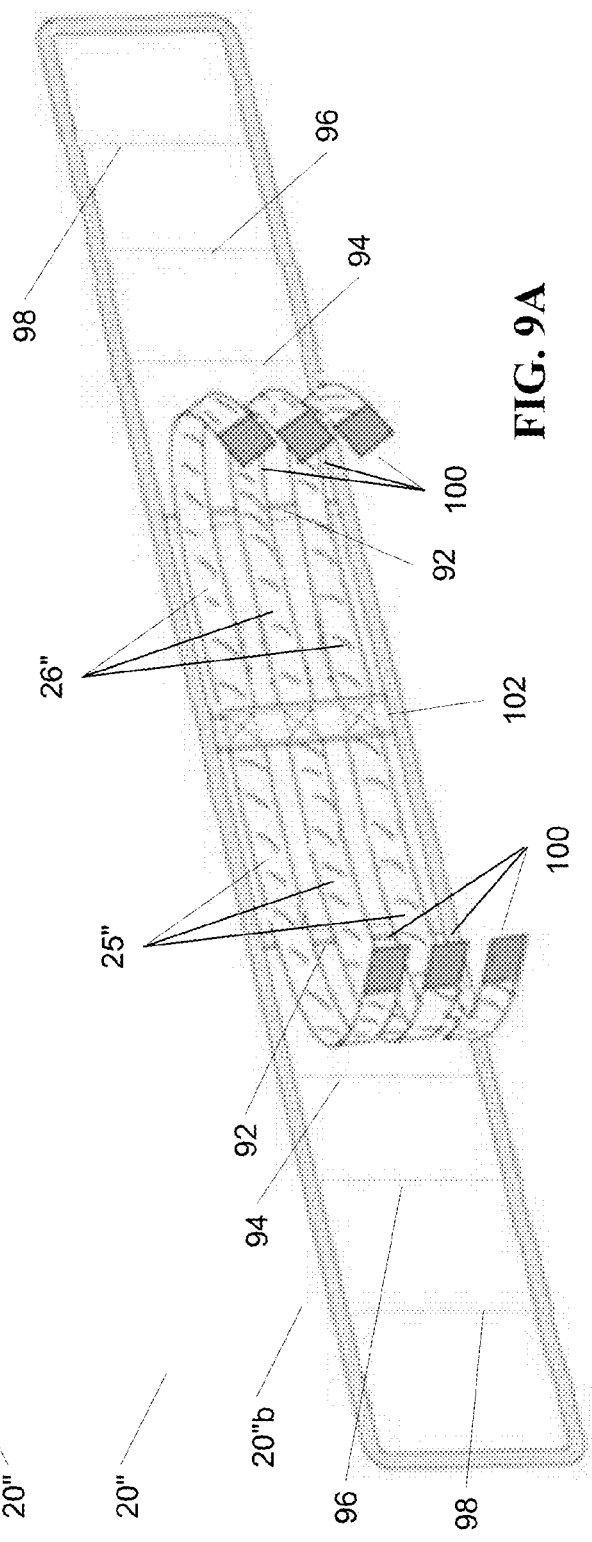
FIG. 9
FIG. 9A

COMPRESSION VEST FOR PATIENTS UNDERGOING HEMODIALYSIS AND IN CRITICAL CARE

CROSS-REFERENCE TO RELATED APPLICATION

This application is continuation-in-part of U.S. patent application Ser. No. 12/977,574, filed Dec. 23, 2010 (now issued as U.S. Pat. No. 9,155,541), which, in turn, is a continuation-in-part of U.S. patent application Ser. No. 12/062,944, filed April 4, 2008 (now issued as U.S. Pat. No. 7,879,069), which, in turn, claims the priority benefit of U.S. Provisional Patent Application No. 61/000,436, filed Oct. 26, 2007, the disclosures of each of these applications are incorporated herein by reference in their entirety.

FIELD

This application relates generally to medical devices and procedures, and more particularly, to medical devices, procedures and treatments used during hemodialysis or on a critical care patient.

BACKGROUND

Patients suffering from renal failure of the kidneys are often treated using hemodialysis procedures to remove excess fluid and metabolic wastes (e.g., urea, creatinine, etc.) accumulated in body tissue and blood. During hemodialysis, a patient's blood is shunted from the body through a hemodialysis machine for diffusion and ultrafiltration before being returned to the patient's circulation system. Hemodialysis treatments are typically performed three or perhaps four times per week on a patient having chronic renal failure, with each session lasting between three to five hours.

Patients undergoing hemodialysis treatment are prone to suffer from hypotensive (low blood pressure) symptoms, such as headache, dizziness, muscle cramping and vomiting. Despite the many improvements made to modern hemodialysis procedures, intradialytic hypotension in hemodialysis patients continues to be a major source of concern for the well being of the patient. Many hemodialysis patients experience chronic hypotension, which is abnormal decrease in the patients' blood pressure. For some of these patients, the intradialytic hypotensive symptoms are so severe that they cannot tolerate the hemodialysis procedure and must instead resort to peritoneal dialysis or renal transplant. Indeed, repeated development of these hypotensive symptoms is a key factor leading to the high mortality rate of hemodialysis patients.

For many hemodialysis patients, it is believed that the intradialytic hypotensive symptoms result from the pooling of blood within the internal organs in the abdominal area or waist of the hemodialysis patient. Some have proposed use of an inflatable abdominal band to improve orthostatic hypotension, which is associated with a decrease in systolic blood pressure when patients change from supine to standing position. For instance, N. Yamamoto et al., Treatment of post-dialytic orthostatic hypotension with an inflatable abdominal band in hemodialysis patients, KIDNEY INTERNATIONAL, 70:1793-1800 (Sep. 27, 2006), discloses use of an inflatable abdominal band to treat patients, who after their hemodialysis treatment, are suffering from post-dialytic orthostatic hypotension. H. Tanaka et al., Treatment of orthostatic intolerance with inflatable abdominal band, THE LANCET, 349:175 (Jan. 18, 1997), discloses use of an inflatable abdominal band to treat orthostatic hypotension in patients with orthostatic intolerance. A. Smit et al., Use of lower abdominal compression to combat orthostatic hypotension in patients with autonomic dysfunction, CLIN AUTON RES 14:167-175 (2004), discloses use of an elastic abdominal binding to increase standing blood pressure in patients with neurogenic orthostatic hypotension. J. Deng et al., Efficacy of compression of different capacitance beds in the amelioration of orthostatic hypotension, CLINICAL AUTONOMIC RESEARCH 7, 321-326 (1997), discloses use of compression garments such as an antigravity suit (G suit) in treating patients with chronic symptomatic orthostatic hypotension.

Other types of compressive devices are known in the art. For instance, U.S. Pat. No. 4,925,133 entitled "Hydraulic Buoyancy Force Suit" discloses a buoyancy force suit to reduce pooling of blood with the goal of maintaining consciousness of flying pilots. U.S. Pat. No. 4,534,338 entitled "Servo Operated Anti-G Suit Pressurization System" discloses a servo operated system for quickly pressurizing an aircraft pilot's anti-G suit during high energy maneuvers. U.S. Pat. No. 4,938,208 entitled "Full Length Compressible Sleeve" discloses a sleeve for applying compressive pressure against a patient's limb to prevent pooling of blood in a patient's limb. Similarly, arterial pressure sphygmomanometers include an inflatable compression band worn about a patient's arm to identify diastolic and systolic arterial pressure. Non-inflatable work wear or belts that wrap around a person's waist are used to reduce the load on the back by providing additional support for the spine.

None of these references, however, address treatment of intradialytic hypotension occurring during the hemodialysis treatment. It is, therefore, desirable to reduce the pooling of blood in the abdominal organs of the patient during hemodialysis treatments in order to eliminate the development of intradialytic hypotensive symptoms over the course of hemodialysis.

Patients in critical care may also encounter similar problems resulting from trauma or burns. Reducing the pooling of blood in the abdominal organs of such critical care patients can lead to more effective fluid and blood infusion and improve cardiac filling to enhance cardiovascular functions of these seriously ill patients. Therefore, it is also desirable to reduce the pooling of blood in the abdominal organs of critical care patients to make fluid or blood infusion more effective in improving cardiac filling to enhance cardiovascular functions.

SUMMARY

One aspect of the disclosure involves a method of increasing venous return in a hypotensive patient in critical care suffering from blood or fluid loss. The method involves elastically constraining the abdomen of the patient while a) concurrently maintaining mobility of the patient's legs and applying non-pulsating compressive pressure to the internal organs within the abdomen of the patient according to a predefined protocol, and b) infusing a volume of fluid into the patient's bloodstream, such that pooling of blood within the patient's abdominal internal organs and distribution of the infused volume in the abdominal organs are both reduced.

Another aspect of the disclosure involves a method of inhibiting hypotensive symptoms in a patient undergoing a procedure. The method involves elastically constraining the abdomen of the patient throughout the procedure while concurrently maintaining mobility of the patient's legs; and applying non-pulsating compressive pressure to the internal organs within the abdomen of the patient during the procedure with an elastic vest having multiple discrete elastic bands affixed thereto, each of the discrete elastic bands having a free end wherein the total number of free ends comprises at least three free ends, the elastic vest including multiple markings thereon to denote compression levels that will be applied when the free ends are releasably affixed to the elastic vest near the markings, the constraining thereby reducing the pooling of blood within the patient's abdominal internal organs while concurrently allowing for unencumbered movement of the patient's legs during the procedure.

Yet another aspect of the disclosure involves a further method of inhibiting hypotensive symptoms in a patient undergoing a procedure. The method involves elastically constraining the abdomen of the patient throughout the procedure while concurrently maintaining mobility of the patient's legs and applying non-pulsating, compressive pressure to the internal organs within the abdomen of the patient according to a predefined protocol during the procedure, the protocol including monitoring bioimpedance of the abdominal organs of the patient, the patient's blood density and hematocrit, thereby reducing the pooling of blood within the patient's abdominal internal organs while concurrently allowing for unencumbered movement of the patient's legs during the procedure.

Yet another aspect of this disclosure involves a method of treating a hypotensive patient undergoing a treatment. The method involves elastically constraining the abdomen of the patient while a) concurrently maintaining mobility of the patient's legs and applying non-pulsating compressive pressure to the internal organs within the abdomen of the patient according to a predefined protocol, and b) infusing a volume of fluid into the patient's bloodstream, such that pooling of blood within the patient's abdominal internal organs and distribution of the infused volume to the abdominal organs are both reduced.

Yet another aspect of this disclosure involves a further method of treating a hypotensive patient undergoing a treatment. The method involves elastically constraining the abdomen of the patient while concurrently maintaining mobility of the patient's legs and applying non-pulsating, compressive pressure to the internal organs within the abdomen of the patient according to a predefined protocol while the treatment is in progress. The protocol includes monitoring one or more bio-indicator measurement parameters and applying the compressive pressure based upon the bio-indicator measurement parameters, thereby inhibiting the hypotensive symptoms while concurrently allowing for unencumbered movement of the patient's legs while the treatment is in progress.

These aspects and advantages arising from the present disclosure will be apparent to those of ordinary skill in the art by reference to the following detailed description and the accompanying drawings.

BRIEF DESCRIPTION OF THE DRAWINGS

FIG. 9 is a plan view of the inner surface of a further example embodiment of the compression vest;

FIG. 9A is a perspective view illustrating the outer surface of the compression vest of FIG. 9;

DETAILED DESCRIPTION

An anti-pooling/compression wear or vest 10 is disclosed herein for preventing the pooling of blood or other fluids in the organs within the abdomen or waist of a patient. The vest 10 may be used for a variety of medical purposes, including, but not limited to, countering the development of intradialytic hypotensive symptoms in patients undergoing hemodialysis and/or improving cardiac filling to enhance cardiovascular functions in critical care patients suffering from trauma or burns. As used herein, the terms "treatment" and "procedure" are used interchangeably and intended to interchangeably mean any or all of these as well as dealing with or preventing hypotensive symptoms in general. This disclosure also includes methods and protocols to pressurize the patient's abdominal organs to one or more preset or predetermined pressures during and after the treatment, designs of the vest 10 to best-fit patient's abdominal contour, and safety features of the vest 10 for the patient's well being.

Vest With Manual Operation

Figure 1:
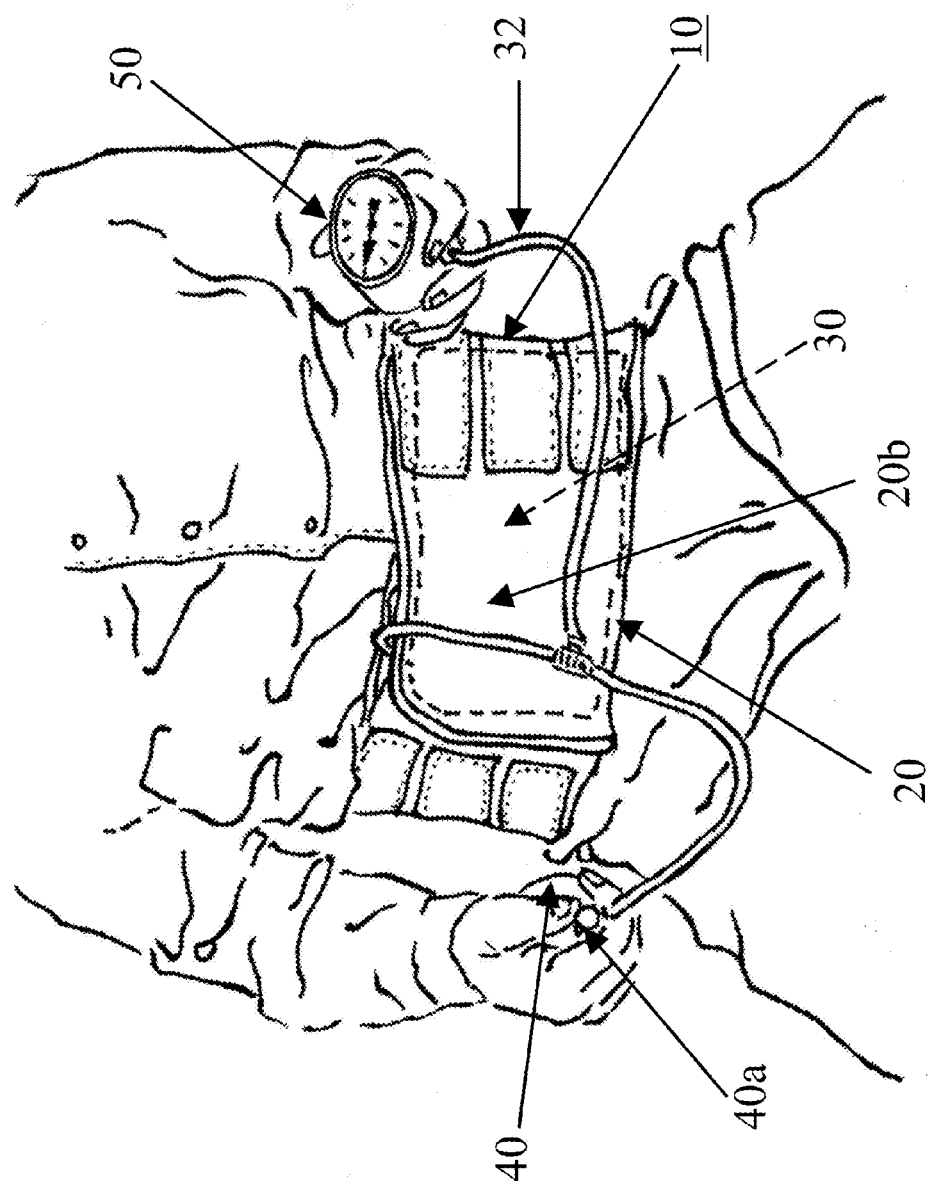
FIG. 1 illustrates an example compression/anti-pooling vest worn around the waist of a patient in accordance with the present disclosure.

FIG. 1 illustrates an example of the anti-pooling/compression wear or vest 10 worn around the waist or abdomen of a patient. The vest 10 includes a flexible band 20 and an inflatable bladder 30 with tubing 32 that may be pressurized using a manual pressurization system 40. An automatic pressurization system, such as the system described further below and illustrated in FIGS. 6-8, may be substituted for the manual pressurization system 40.

Figure 1A:
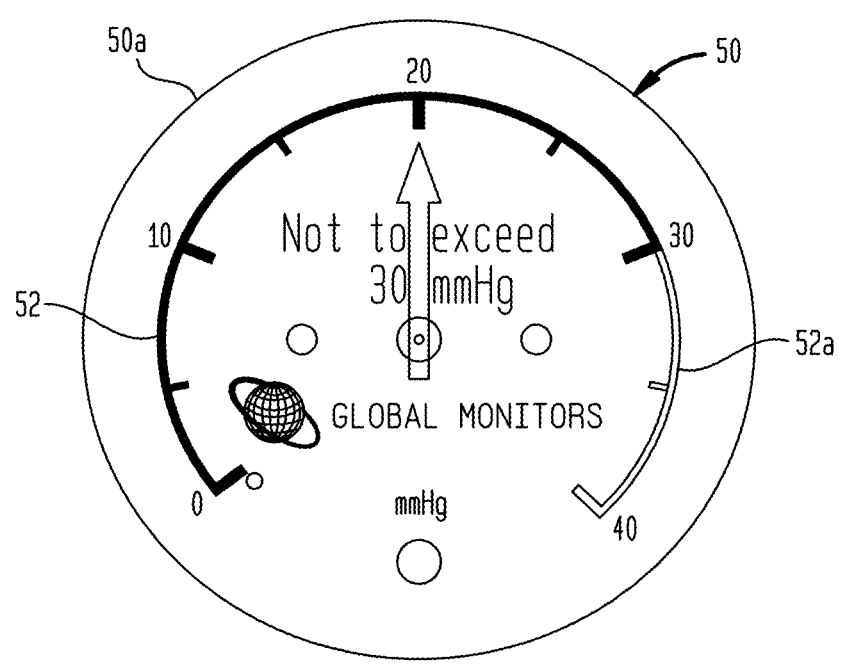
FIG. 1A illustrates the dial of a pressure gauge utilized with the compression vest illustrated in FIG. 1.

A patient is illustrated in FIG. 1 squeezing a manual pump or bulb 40 to increase pressure in the inflatable bladder 30, which is located within the vest 10. The pressure within the inflatable bladder 30 is displayed on a pressure dial or gauge 50, which is shown in FIG. 1 as being held in the patient's other hand. A dial 50a of the pressure gauge 50 is illustrated in FIG. 1A. The dial 50a includes a plurality of markings indicative of pressure in, for example, mm Hg, with a region 52a of the markings being highlighted to indicate that pressure above a preset or predetermined maximum threshold (e.g., above 30 mm Hg) for use with the anti-pooling vest 10. To ensure proper use of the vest 10, instruction labels may be provided on the vest 10, as well as a nametag for the patient and/or health care professional to write the patient's name.

Figure 2:
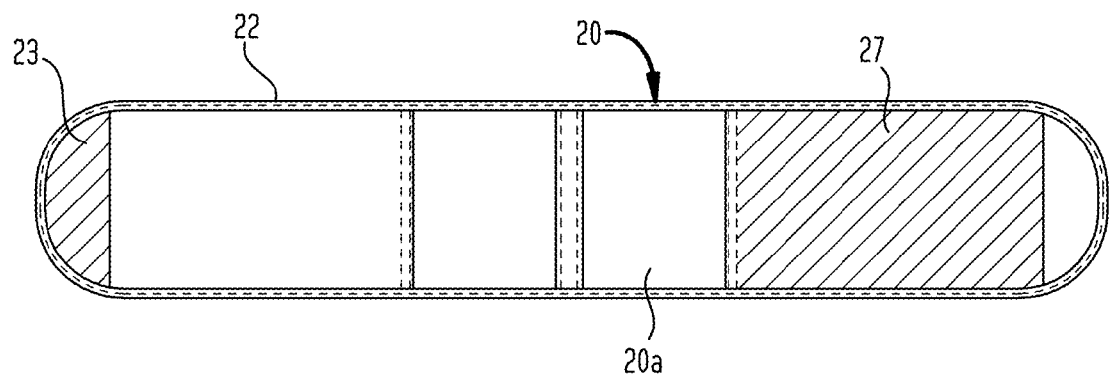
FIG. 2 is a plan view of the inner surface of one example embodiment of the compression vest illustrated in FIG. 1.
Figure 2A:
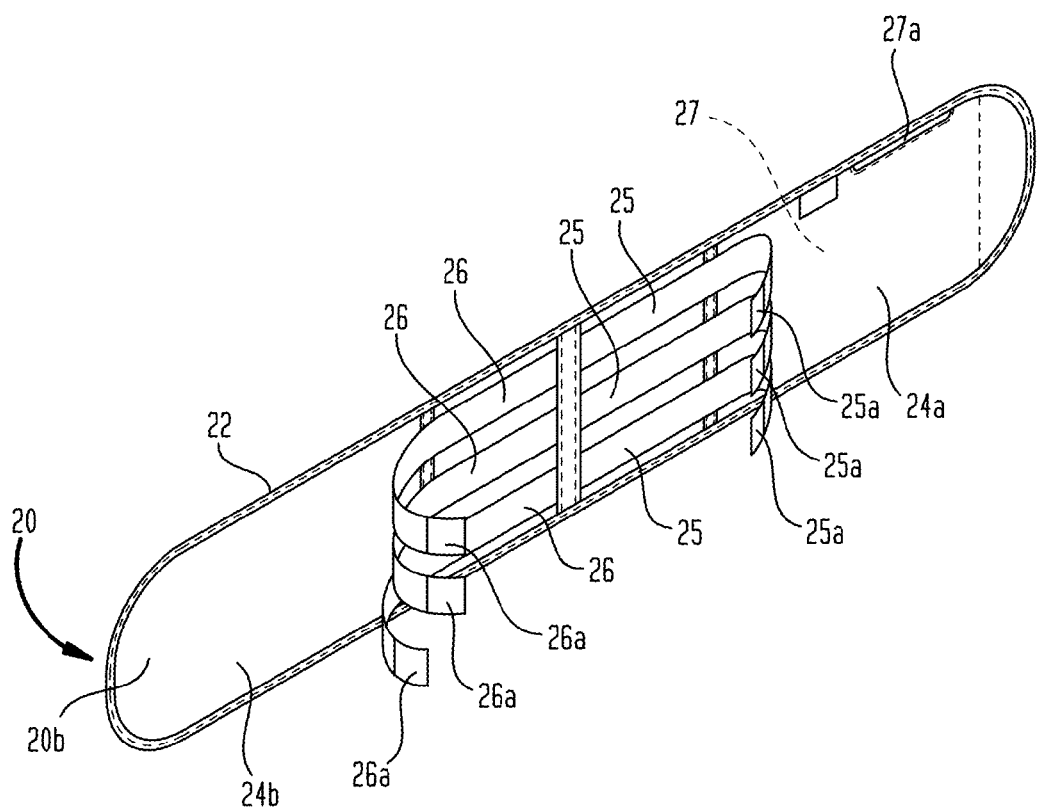
FIG. 2A is a perspective view illustrating the outer surface of the compression vest shown in FIG. 2.

One example embodiment of the band 20 is illustrated in FIGS. 2 and 2A. The band 20 is flexible so that it can be wrapped about the abdomen or waist of the patient. The band 20 is typically made of nylon, such as, for example, polyurethane coated 420d Nylon fabric (420D/PU2 Nylon). Alternatively, the band 20 may be made from other suitable non-stretchable fabrics. The band 20 may be, for example, approximately eight to ten inches wide and approximately 55 inches in length. The size of the band, its material and its color may be modified to fit the need or preference of the patient.

The inner or back surface 20a of the band 20 is illustrated in FIG. 2. This is the surface 20a that contacts the patient when the band 20 is wrapped about the abdomen or waist of the patient as illustrated in FIG. 1. A webbing trim 22, such as, for example, a ⅞ inch polypropylene (PP) webbing trim, may be provided around the edges of the band 20. The inner surface 20a of the band 20 includes an area 23 provided with a plurality of fasteners, such as Velcro® brand hook fasteners, for releasably engaging corresponding fasteners, such as Velcro® brand loops 24a, 24b, located on the front surface 20b of the band 20.

The front or outer surface 20b of the band 20 is illustrated in FIG. 2A. The outer surface 20b is the surface of the band 20 that is exposed when the band is wrapped about the abdomen or waist of a patient as illustrated in FIG. 1. The outer surface 20b includes an area 24a, 24b containing a plurality of fasteners, such as Velcro® brand loops. When the band 20 is wrapped about the abdomen or waist of a patient with the inner surface 20a in contact with the patient as is shown in FIG. 1, the band may be releasably held in place by bringing the area 23 containing the plurality of hook fasteners into contact with the corresponding loops in the area 24a on the outer surface 20b of the band. It is understood that the arrangement of hook and loop fasteners may be reversed so that the loop fasteners are arranged in area 23 and the hook fasteners in area 24a, 24b.

The band 20 also includes one or more elastic bands or strips 25, 26, each strip having one end that is sewn or otherwise affixed to the outer surface 20b of the band 20 and an opposing end that is free from the outer surface. A fastener 25a, 26a, such as one part of a Velcro® brand hook and loop fastener, is connected to the free end of each of the elastic strips 25, 26. Each elastic strip 25, 26 is between about 1.75 and about 3 inches wide. In the embodiment illustrated in FIGS. 2 and 2A, the band 20 includes three spaced apart, elastic strips 25 having their free end with the fastener 25a extending in the direction of area 24a and three spaced apart, elastic strips 26 having their free end with the fastener 26a extending in the direction of area 24b. The use of three pairs of elastic strips 25, 26 makes the band 20 more closely conform to the body contour of the patient for more effective compression of internal organs and provides a greater safety margin for the patient not to be overly compressed. It is understood, however, that the use of three pairs of elastic strips 25, 26 is exemplary and that the band may incorporate a greater number or lesser number of elastic strips 25, 26 than illustrated in the drawings.

As discussed above, the band 20 is first wrapped about the abdomen or waist of a patient to enclose most of the patient's internal organs. The band 20 is releasably held in place by bringing the area 23 containing the plurality of hook fasteners into contact with the corresponding loops in the area 24a on the outer surface 20b of the band. To better conform the band 20 to the contour of the patient's waist, the free end of each elastic strip 25 is stretched in the direction of area 24a and the free end of each elastic strip 26 is stretched in the direction of area 24b. When sufficient tension is placed on each strip to better conform the band 20 to the contour of patient's waist, then the elastic strips 25, 26 are releasably connected to the band by engaging the hook fasteners 25a, 26a on the free ends of the strips with the corresponding loop fasteners located in the areas 24a and 24b on the outer surface 20b of the band.

The band 20 also may include a pouch or pocket 27 having an opening 27a through which the inflatable bladder 30 inserted for placement within the pocket 27. Alternatively, the inflatable bladder 30 may be an integral part or otherwise built into the band 20. In this embodiment, the opening 27a is approximately five inches in length and the pocket 27 is approximately 19 inches in length to accommodate a 16 inch by seven inch inflatable bladder 30. The inside of the pocket 27 is typically made from nylon, such as, for example, polyurethane coated 210d Nylon fabric (210D/PU2 Nylon). When the vest 10 is properly fitted on the patient and the inflatable bladder 30 in the pocket 27 is pressurized, the elastic straps 25, 26 and Velcro® brand hook and loop fasteners ensure uniform pressure compression of the patient's internal organs.

Figure 3:
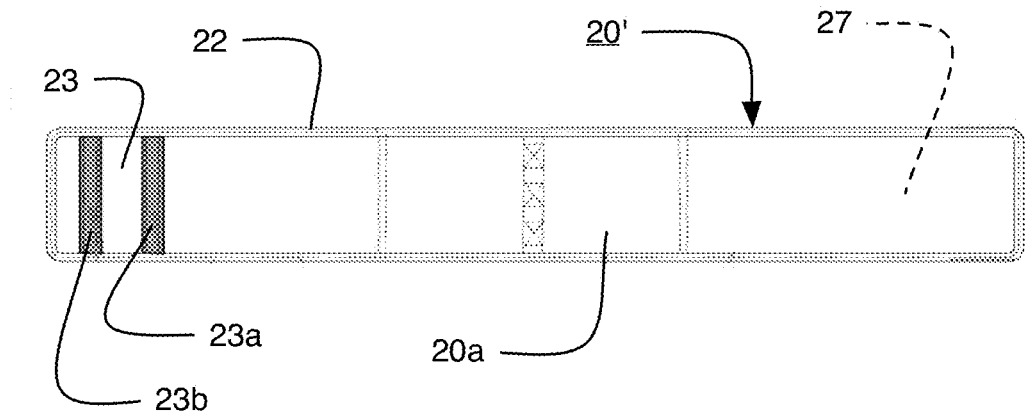
FIG. 3 is a plan view of the inner surface of another example embodiment of the compression vest.
Figure 3A:
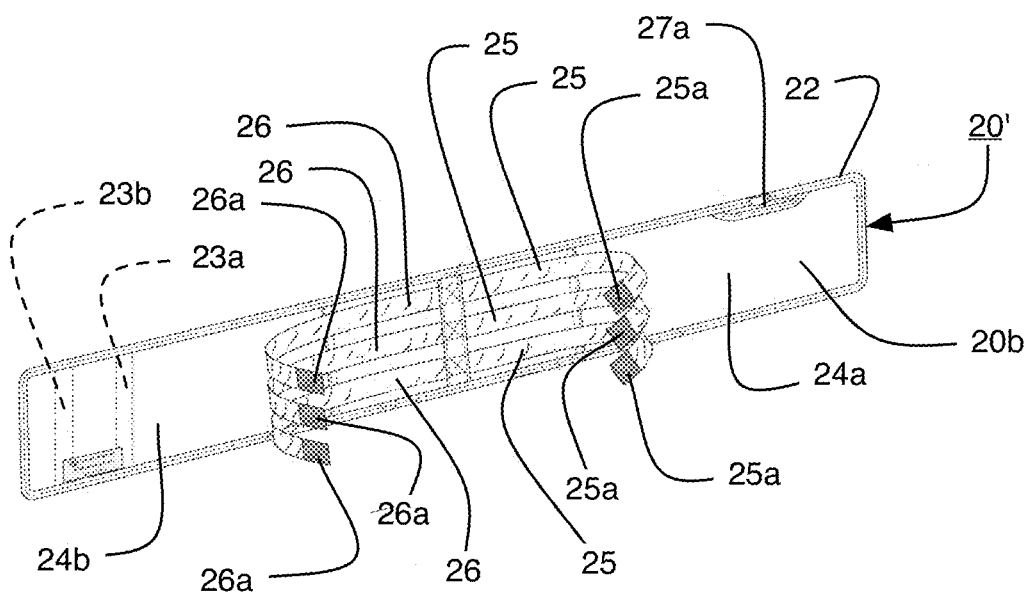
FIG. 3A is a perspective view illustrating the outer surface of the compression vest shown in FIG. 3.

Another example embodiment of the band 20' is illustrated in FIGS. 3 and 3A. The band 20' is similar to the band 20 illustrated in FIGS. 2 and 2A, with the exception that two strips 23a, 23b of fasteners, such as Velcro® brand hook fasteners, are provided in the area 23. These strips 23a, 23b may be affixed to the band 20' in a conventional manner, such as, for example, by sewing and/or using an adhesive. When the band 20' is wrapped about the abdomen or waist of a patient with the inner surface 20a in contact with the patient as is shown in FIG. 1, the band may be releasably held in place by bringing the two strips 23a, 23b of hook fasteners into contact with the corresponding loops in the area 24a on the outer surface 20b of the band. The construction and operation of the band 20' is similar to the band 20 described above in all other material respects.

Figure 4:
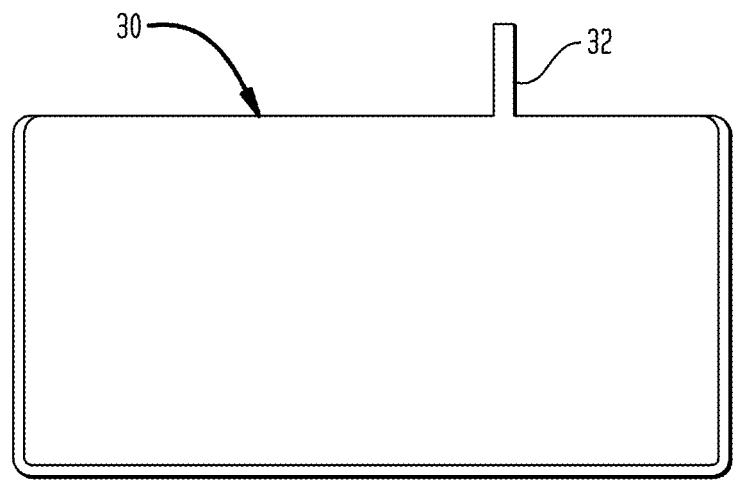
FIG. 4 illustrates an inflatable bladder utilized with the compression vest illustrated in FIG. 1.

An example inflatable bladder 30 is illustrated in FIG. 4. The bladder 30 is typically made of flexible polyvinyl chloride (PVC), rubber or other impermeable materials that can be inflated without air leakage. As discussed above, the bladder 30 is inserted through the opening 27a in the band 20, 20' to fit snugly to the pocket 27. Alternatively, the bladder 30 may be an integral part or otherwise built into the band 20. The bladder 30 may be, for example, a PVC sheet of 16 inches by fourteen folded to form a dimension of 16 inches by seven inches with three sides heat sealed. Other configurations of the bladder 30 may also be used with the anti-pooling vest 10. Hollow, flexible tubing 32 extends from the bladder 30 to provide a fluid conduit to the pressurization system, pressure gauge and optional alarm.

Figure 4A:
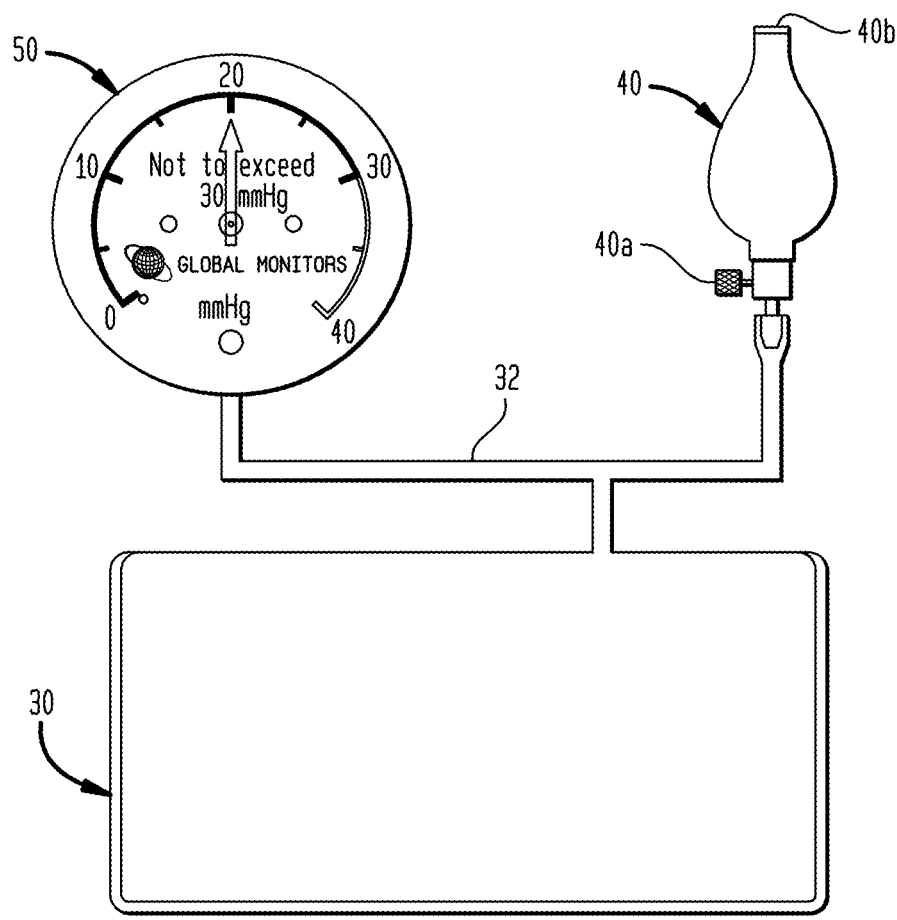
FIG. 4A illustrates the configuration of the inflatable bladder, tubing, manual pressurization system and pressure gauge utilized with the compression vest illustrated in FIG. 1.

FIG. 4A illustrates an exemplary configuration of the inflatable bladder 30, tubing 32, manual pressurization system 40 and pressure gauge 50 utilized with the vest 10. The manual pressurization system includes a bulb or manual pump 40, a pressure release valve 40a, a pressure gauge 50, and an optional alarm (not shown). As illustrated in FIG. 1, the tubing 32 from the inflatable bladder 30 is joined through a T-joint or other connector to the tubing 32 connected to the bulb 40 and pressure gauge 50. The functions of these components are described next.

When the pressure release control valve 40a of the bulb or manual pump 40 is set to the closed position, the repeated hand squeeze of the bulb by the patient or health care professional causes the bladder 30 to inflate to a predetermined, preset or desired pressure level as indicated by the pressure gauge 50. By turning the control valve 40a to the open position, the pressurized air in bladder 30 is released and the pressure in the bladder can return to zero. A one-way control valve 40b at the distal opening or air inlet of the bulb 40 only permits ambient air to enter the bulb 40 and flow from the bulb 40 as it is squeezed through the pressure release control valve 40a to inflate the bladder 30. When the bulb 30 is relaxed and returns to its normal configuration, air is allowed to flow through the one-way valve 40b from the atmosphere to fill up the bulb.

The pressure gauge 50 displays the pressure in the bladder 30, which corresponds to the pressure being imposed on the internal organs of the patient when the anti-pooling vest 10 is worn by the patient. A safety pressure release valve (not shown) may be incorporated into the pressure gauge 50 or elsewhere in the pressurization system to limit the maximum pressure that can be imposed by the anti-pooling vest 10 on the patient's waist and internal organs. Normally, the maximum pressure to inflate the bladder 30 would not exceed 20 mm Hg. Accordingly, the safety pressure release valve could be set to automatically open and release pressure in the bladder 30 that exceeds, for example, 30 mm Hg or 40 mm Hg.

An optional alarm may also be used with the vest 10 to make an audible sound at preset or predetermined time intervals to remind the health care professional and/or patient that it may be time to adjust the inflation pressure of the bladder 30 according to, for example, the pressurization protocols described herein.

Manual Pressurization And Depressurization Protocol

Prior to starting the hemodialysis treatment, the vest 10 is placed about the abdomen or waist of the patient in the manner described above. Once the hemodialysis process is initiated with the patient, one course of pressurization of the inflatable bladder 30 will be a step increase of the pressure by about 3 to 5 mm Hg every half an hour of treatment.

Figure 5:
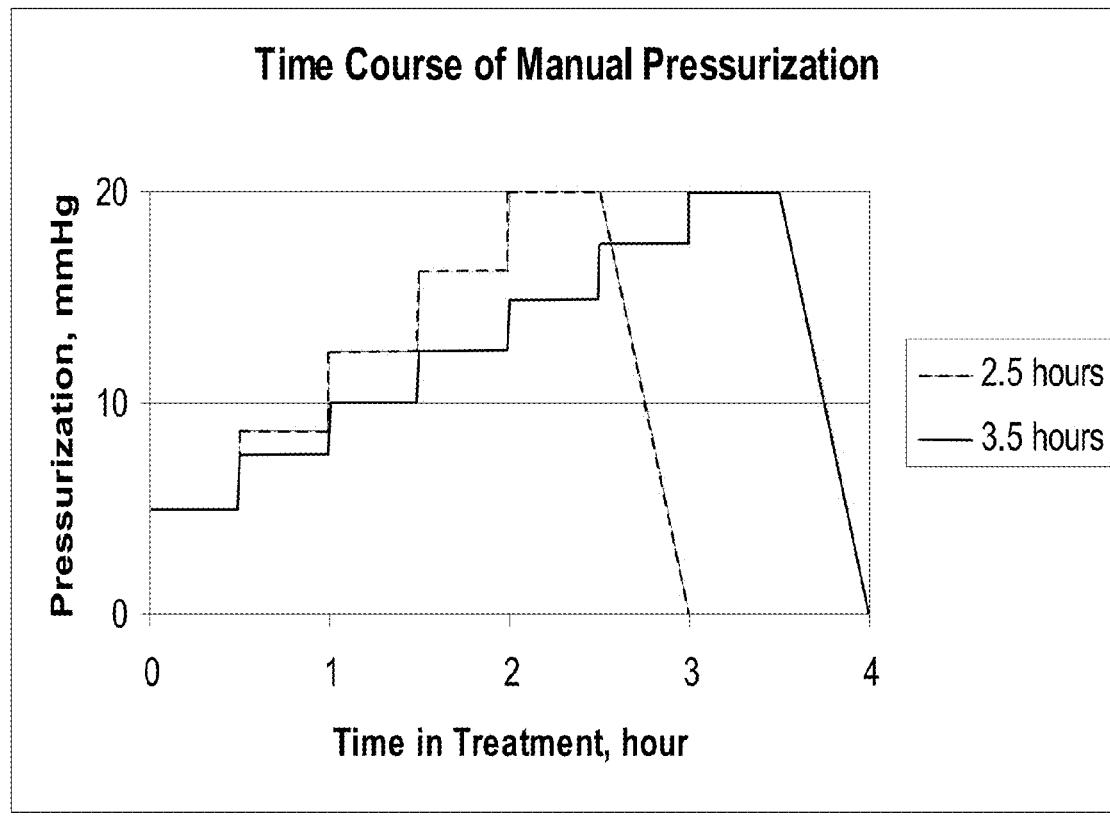
FIG. 5 is a graph illustrating manual pressurization of the compression vest over time during a hemodialysis treatment.

Two illustrative examples of manual pressurization protocols are illustrated in FIG. 5. The first manual pressurization protocol illustrated in FIG. 5 is for a hemodialysis treatment period of approximately 2.5 hours. Prior to commencing hemodialysis treatment, the bladder 30 worn about the patient's abdomen or waist is inflated to a predetermined or preset pressure of about 5 mm Hg by manually squeezing the bulb or pump 40 and the pressure is maintained at this level for about 30 minutes. The pressure in the bladder 30 is then increased to a second predetermined or preset pressure of about 9 mm Hg by manually squeezing the bulb or pump 40 and maintained at this level for about 30 minutes. After about an hour of treatment, the pressure in the bladder 30 is again increased to a third predetermined or preset pressure of about 12 mm Hg by manually squeezing the bulb or pump 40 and maintained at this level for another 30 minutes. After about 1.5 hours of treatment, the pressure in the bladder 30 is again increased to a fourth predetermined or preset pressure of about 16 mm Hg by manually squeezing the bulb or pump 40 and maintained at this level for 30 minutes. After about two hours of treatment, the pressure in the bladder 30 is increased to a fifth predetermined or preset pressure of about 20 mm Hg by manually squeezing the bulb or pump 40 and maintained at this pressure until the 2.5 hour treatment is completed. Once the 2.5 hour treatment period is completed, the patient continues to wear the pressurized anti-pooling vest 10 for at least 30 minutes to an hour. During this time, the pressure in the bladder 30 is gradually reduced to zero using the pressure relief valve 40a to allow the blood volume in the patient's internal organs to gradually return to desirable levels without hypotension. Thereafter, the depressurized vest 10 may be removed from the patient.

The second manual pressurization protocol illustrated in FIG. 5 is for a hemodialysis treatment period of approximately three hours. Prior to commencing hemodialysis treatment, the bladder 30 worn about the patient's abdomen or waist is inflated to a predetermined or preset pressure of about 5 mm Hg by manually squeezing the bulb or pump 40 and the pressure is maintained at this level for about 30 minutes. The pressure in the bladder 30 is then increased to a second predetermined or preset pressure of about 7.5 mm Hg by manually squeezing the bulb or pump 40 and maintained at this level for about 30 minutes. After about an hour of treatment, the pressure in the bladder 30 is again increased to a third predetermined or preset pressure of about 10 mm Hg by manually squeezing the bulb or pump 40 and maintained at this level for another 30 minutes. After about 1.5 hours of treatment, the pressure in the bladder 30 is again increased a fourth predetermined or preset pressure of to about 12.5 mm Hg by manually squeezing the bulb or pump 40 and maintained at this level for 30 minutes. After about two hours of treatment, the pressure in the bladder 30 is increased to a fifth predetermined or preset pressure of about 15 mm Hg by manually squeezing the bulb or pump 40 and maintained at this pressure for 30 minutes. After about 2.5 hours of treatment, the pressure in the bladder 30 is again increased to a sixth predetermined or preset pressure of about 17.5 mm Hg by manually squeezing the bulb or pump 40 and maintained at this level for 30 minutes. After about three hours of treatment, the pressure in the bladder 30 is increased to a seventh predetermined or preset pressure of about 20 mm Hg by manually squeezing the bulb or pump 40 and maintained at this pressure until the 3.5 hour treatment is completed. Once the 3.5 hour treatment period is completed, the patient continues to wear the pressurized vest 10 for at least 30 minutes to an hour. During this time, the pressure in the bladder 30 is gradually reduced to zero using the pressure relief valve 40a to allow the blood volume in the patient's internal organs to gradually return to desirable levels without hypotension. Thereafter, the depressurized vest 10 may be removed from the patient.

Vest With Automatic Operation

Figure 6:
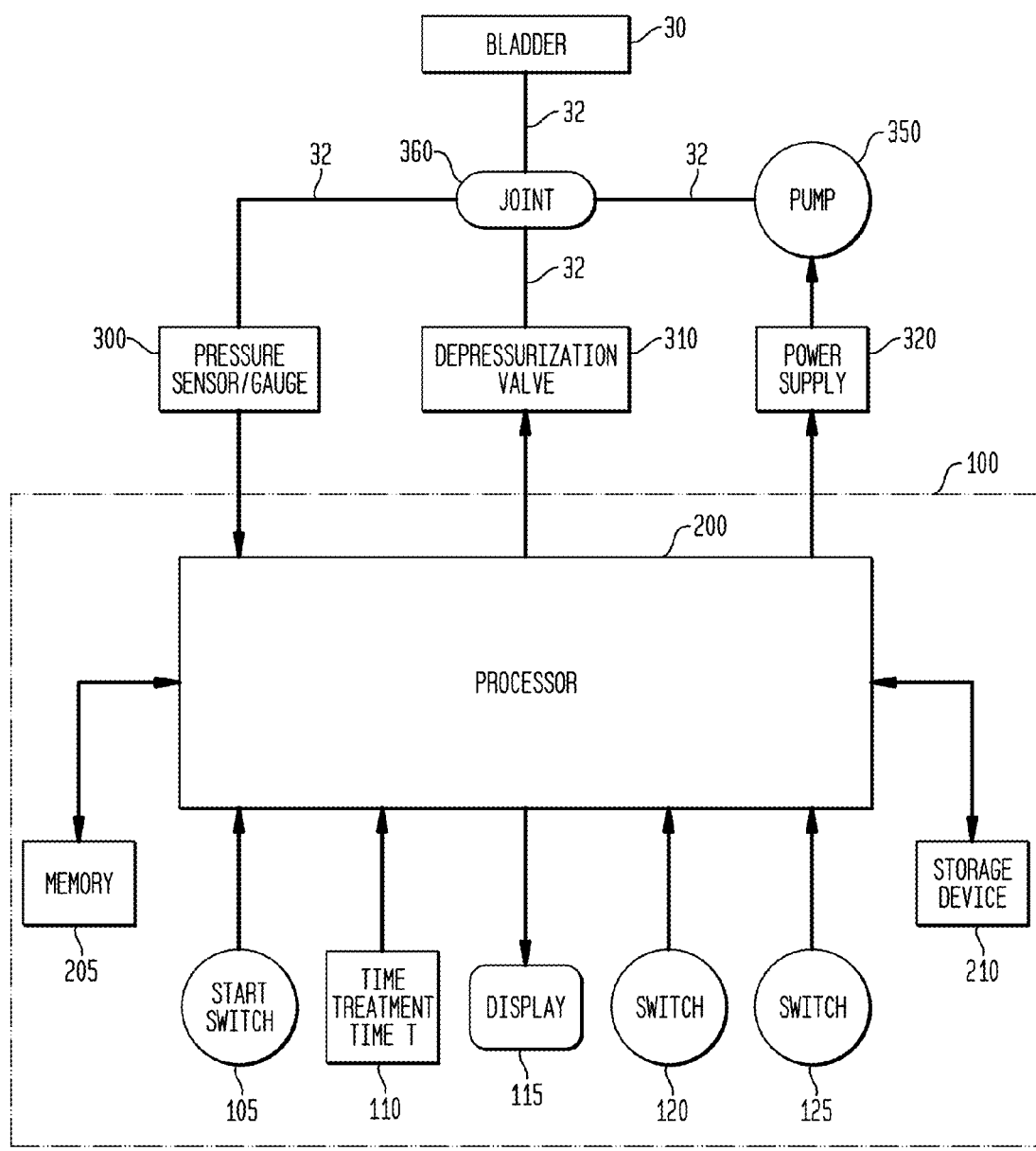
FIG. 6 is a schematic diagram of an automatic pressurization controller for pressurizing or depressurizing the inflatable bladder of the compression vest.

The vest 10 may also be utilized with an automatic, programmable pressurization/depressurization system. A schematic diagram of an example automatic, programmable system for pressurizing or depressurizing the inflatable bladder 30 of the vest 10 is illustrated in FIG. 6. The bladder 30 in the vest 10 may be inflated to predetermined, preset or desired pressures during and after the treatment in accordance with pressurization/depressurization protocols that correspond to the length of treatment and maximum desired pressure that have been selected by the physician and/or health care professional. The band 20, 20' and inflatable bladder 30 in the vest with automatic operation is identical in all material respects to that of the vest 10 described above with manual operation.

In the example embodiment illustrated in FIG. 6, the inflatable bladder 30 in the vest 10 worn about the patient's abdomen or waist is connected by tubing or conduit 32 to an air pump 350, a depressurization valve 310, and a pressure sensor/gauge 300. A four way joint, pipe connector or other conventional fitting 360 may be utilized to facilitate fluid connection of the pump 350, depressurization valve 310, and pressure sensor/gauge 300. The pump 350 is an electric pump that is powered by a pump power supply 320 and capable of generating sufficient air pressure to inflate the bladder 30 to the desired inflation pressure. When the pump 350 and depressurization valve 310 are not activated, no communication occurs between the joint 360 and atmosphere. For increased safety to ensure that the patient is not overly compressed by the automatic pressurization system, the pump 350 and its associated power supply 320 should have the characteristic that the maximum deliverable pressure at zero flow is less than a preset or predetermined value.

The automatic pressurization/depressurization system also includes a controller 100 for controlling the pump 350 (and associated pressurization of the bladder 30) and the depressurization valve 310 to automatically achieve the desired pressurization/depressurization protocol, which will be discussed below with respect to FIG. 8. The controller 100 includes a processor 200 (e.g., central processing unit ("CPU"), a memory 205 (e.g., random access memory ("RAM") and/or read only memory ("ROM")), and a storage device 210 (e.g., hard disk drive, compact disk drive, etc.). Various input/output devices are connected to the processor 200, such as a display 115, start switch 105, timer 110, treatment period setting switch 120, maximum pressure setting switch 125, and pressure sensor/gauge 300.

Figure 7:
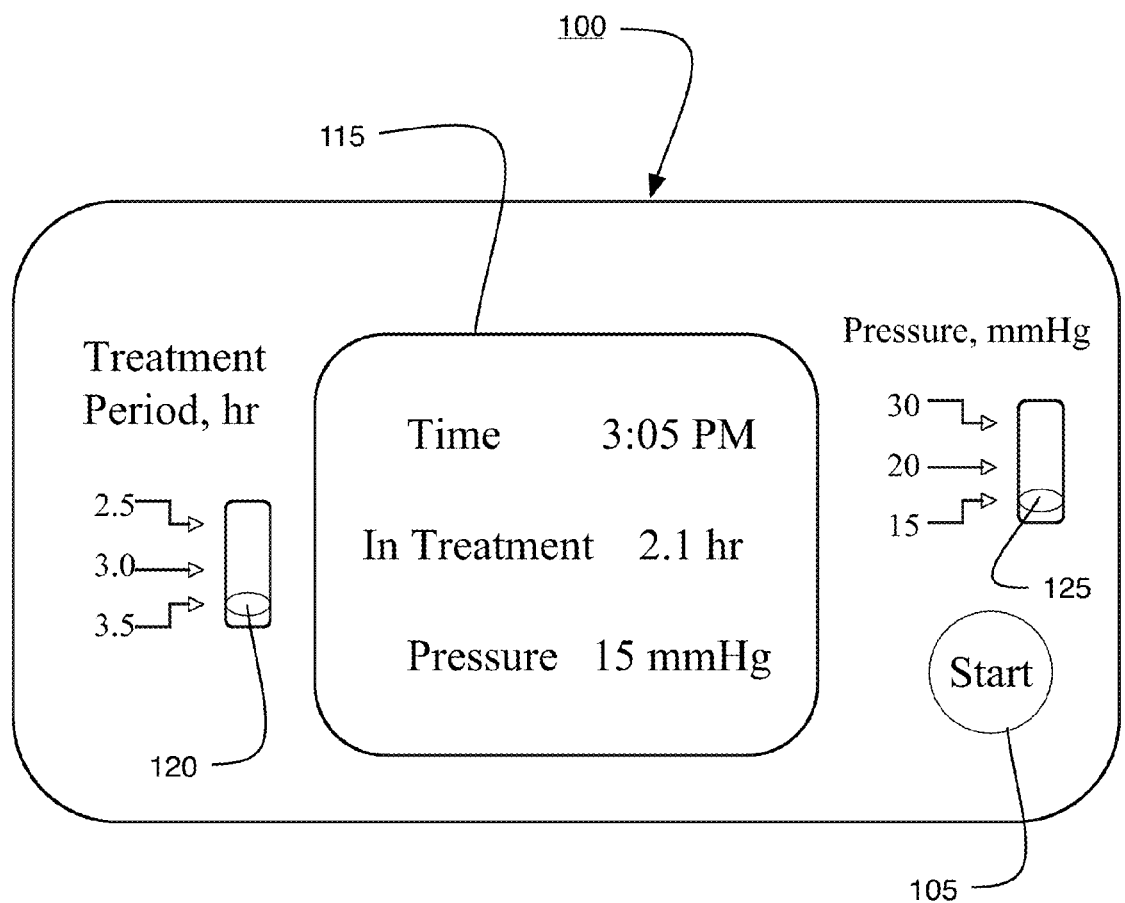
FIG. 7 illustrates an example display on an automatic pressurization controller for the compression vest.

A display 115 on the automatic pressurization controller 100 for the vest 10 is illustrated in FIG. 7. The controller 100 includes a start switch 105, treatment period setting switch 120, and maximum pressure setting switch 125. The physician or health care professional can activate the controller 100 and turn power on to all units in the controller by depressing the start switch 105.

Prior to starting the hemodialysis treatment using the automatic pressurization system, the vest 10 is placed about the abdomen or waist of the patient in the manner described above. The physician or other health care professional can select the treatment period for pressurization of the inflation bladder 30 by moving the selector switch 120 to the desired time interval (e.g., 2.5 hours, 3.0 hours, 3.5 hours, etc.). Similarly, the physician or other health care professional can select the maximum pressure to inflate the bladder 30 by moving the selector switch 125 to the desired maximum pressure (e.g., 15 mm Hg, 20 mm Hg, 30 mm Hg, etc.). It is understood that the number and value of the selector switch positions illustrated in FIG. 7 are exemplary and that this disclosure is not intended to be limited to the specific switch or a specific number of positions and/or values associated with those positions illustrated in the drawings.

The processor 200 is pre-programmed with a pressurization/depressurization protocol for each combination of time interval and maximum pressure settings of the switches 120, 125. Exemplary pressurization/depressurization protocols are discussed further below with respect to FIG. 8.

The display 115 displays the current time, the time in treatment T, and the actual measured pressure P in the inflatable bladder 30 as measured by the pressure sensor/gauge 300. The timer 110 keeps the current time and records the time in treatment T, which information is communicated to the processor 200 and is also displayed on the display 115.

The processor 200 derives the pressure P in the inflatable bladder 30 (without the oscillation associated with respiration) by averaging the pressure output from the pressure sensor/gauge 300. This ensures that pressure fluctuation due to the patient's breathing is removed. The pressure sensor/gauge 300 measures the actual pressure P in the inflatable bladder 30 and sends a signal associated with the measured pressure P to the processor 200 to determine when to activate the pump 350 and/or depressurization valve 310. The processor 200 executes the pre-programmed pressurization/depressurization protocol to adjust the pressure P in the inflatable bladder 30 based on the elapsed treatment time T input from the timer 110, the actual pressure P input from the pressure sensor/gauge 300, and the selected treatment period and maximum pressure settings from the switches 120, 125.

If the actual pressure P measured by the pressure sensor/gauge 300 is below the desired pressure, as determined by the pre-programmed pressure protocol, then the processor 200 activates the pump power supply 320 to drive the pump 350 to inflate the bladder 30. When the actual pressure P measured by the pressure sensor/gauge 300 reaches the desired pressure according to the pressure protocol, then the processor 200 deactivates the pump power supply 320 to turn the power off to the pump 350. As a safety feature, the voltage from the power supply 320 can be limited to not exceed a predetermined or preset voltage so that the pressure generated by the pump 350 cannot exceed a predetermined or preset pressure threshold, which is typically a maximum pressure P of 30 mm Hg.

When the elapsed treatment time T measured by the timer 110 exceeds the preset treatment time according to the selected setting of the switch 120, the processor 200 activates the depressurization valve 310 by transmitting a signal to the solenoid on the depressurization valve to open the valve and slowly depressurize the inflatable bladder 30 by venting or otherwise releasing air from the bladder to atmosphere.

Figure 8:
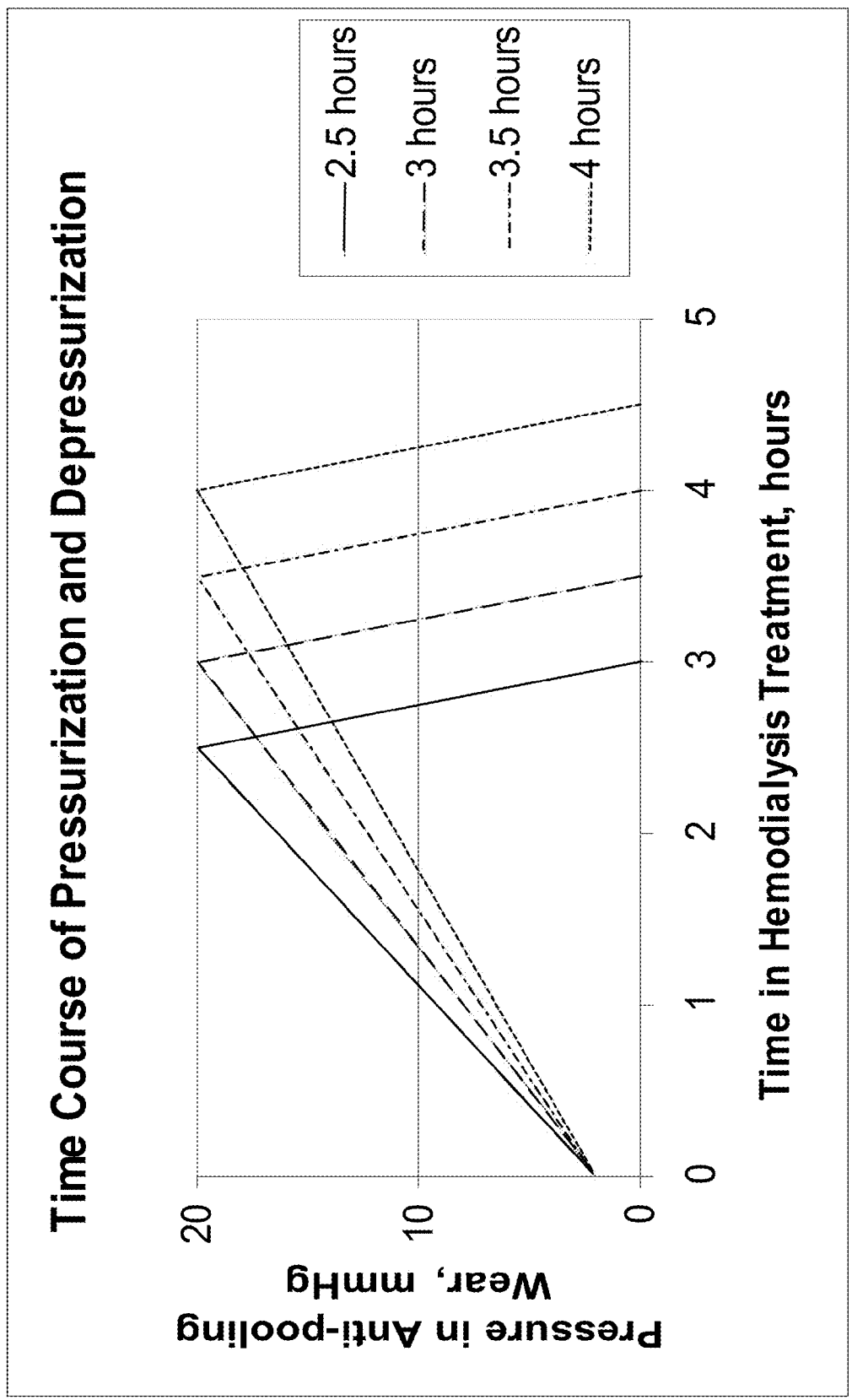
FIG. 8 is a graph illustrating pressurization of the compression vest over time by an automatic pressurization controller during a hemodialysis treatment.

Four exemplary automatic pressurization/depressurization protocols are illustrated in FIG. 8 to show the time course of the pressure to inflate the bladder 30 and thus to generate compression to the patient's abdominal organs. The four exemplary protocols are for a selected maximum pressure of 20 mm Hg for hemodialysis treatment times of 2.5 hours, three hours, 3.5 hours and four hours, respectively. The protocols illustrate a predetermined or preset increase in pressurization of the inflatable bladder 30 over time up to the maximum desired pressure and then the gradual decrease in pressure in the inflatable bladder for at least 30 minutes following the expiration of the hemodialysis treatment time. It is understood that the predetermined or preset inflation pressures correspond to the length of treatment and maximum desired pressure selected by the physician or other health care professional.

A higher compression pressure will reduce the blood volume in the patient's abdominal organs for the improvement of venous return, which will subsequently increase cardiac filling and cardiac output for the alleviation of hypotensive symptoms.

Because the improved venous return will lead to better cardiac filling and subsequently higher cardiac output, the improved cardiovascular functions may allow the physician to prescribe a higher rate of ultrafiltration for the patient during the course of hemodialysis. In this way, the hemodialysis treatment time may be reduced for the removal of the same volume of excess fluid that had been accumulated in the body tissue over the time between the previous hemodialysis treatment and the current one.

Once the patient completes the hemodialysis treatment, the patient would still wear the anti-pooling vest for the depressurization process. This process will allow the patient's cardiovascular system to adjust to the depressurization and to minimize the potential for blood to rapidly pool back to the abdominal organs and subsequently the development of hypotensive symptoms.

The physician could also prescribe the use of vest 10 for home hemodialysis. Its use can shorten the time required to complete home hemodialysis and to reduce the incidence on the development of hypotensive symptoms.

Operation of the Vest for Patients with Trauma or Burns in Hospital's Critical Care Units Because of blood or fluid loss though trauma or burns, these patients are often hypotensive and require infusion of a volume of fluid or blood. Some of the infused fluid or blood volume tends to expand the microcirculation and/or the macrocirculation. It is the latter that would determine the filling of the heart chambers. More cardiac filling would enable the non-damaged heart to increase cardiac output to deliver more blood flow to important organs. With better blood flow, the patient has a better and speedier chance for recovery. During the hypotensive stage, whether in trauma or during hemodialysis, blood vessels may autoregulate for dilatation to allow more blood to flow through the vessel. Advantageously, use of the vest 10 in conjunction with infusion can be used to improve cardiac filling and make the volume expansion more effective for the alleviation of hypotension and/or shock.

Contrary to conventional thinking, this combination approach treats the abdominal organs as being the reason why fluid infusion alone is less effective in countering hypovolemia, hypotension and low cardiac output. Thus, the physician may prescribe the use of the vest 10 for patients capable of accepting abdominal compression to counter the dilatation of blood vessels within the internal organs within the waist or abdomen of the patient for the improvement of venous return during fluid infusion. As a result, the infused blood volume would become more effective to increase venous return, cardiac filling and subsequently cardiac output for the betterment of cardiovascular functions in critical care patients and patients in shock. Similarly, fluid infusion can be used during hemodialysis if the use of the vest 10 alone cannot adequately mitigate the intradialytic hypotension. Thus, by infusing a volume of fluid into the patient's bloodstream while the vest 10 is applying compressive pressure to the patient's abdominal internal organs, pooling of blood within the patient's abdominal internal organs and distribution of the infused volume in the abdominal organs will both be reduced.

A low arterial pressure or low total blood volume is an indication of poor cardiovascular function. The larger the pressurization to be provided by the anti-pooling vest, the greater the shifting of blood from the internal organs toward the heart. Accordingly, the physician may select the level of pressurization to be inversely proportional to either the arterial blood pressure or the total blood volume of the patient.

The physician may order the use of appropriate medication, such as the use of vasoconstrictor eye drops or intramuscle injection, to further complement the anti-pooling function of the vest 10.

Non-Inflatable Configurations

Another alternative example embodiment of the vest includes an alternative band 20" as illustrated in FIGS. 9 and 9A. This example embodiment of the band 20" is not inflatable and is, or includes portions, that are stretchably elastic so that it can be wrapped about the abdomen or waist of the patient and different degrees of stretch can be used to apply differing levels of compressive force to the internal abdominal organs.

In order to accommodate different size and girth people, the band 20" can be provided in different sizes. Table 1 below shows representative example dimensions for the band to accommodate different sized people. It is believed that four sizes should be sufficient for most instances, however, it should be understood that a greater or lesser number of sizes can be used. Note that the columns labeled "a," "b," "c," "d" and "h"" correspond to the similarly labeled dimensions in FIGS. 9 and 9A (not to scale) with the distances under column "a" denoting the locations of marks to be described below. In this example, the total length of any given size band 20" is 6a+2b+c+d for which "a" indicates the distance between edges of the indicator markings and hence it is associated with the % stretching of the elastic band, the distances "b" generally establish the relaxed length of the band, with the location between the two distances "b" denoting a "central" portion 102 of the band 20", which may or may not be the actual center of the band 20". The segments "c" and "d" are of suitable length to provide for reasonable overlapping and wrapping around the waist or abdomen, with the central portion 102 ideally being placed so that it is essentially centered on the lower back. Example dimensions for multiple sizes of two different example implementations for each are also tabulated in Tables 1 and 2. Note that, although Tables 1 and 2 each illustrate four sizes: small, medium, large and extra large, the use of fewer, greater numbers of sizes or other size ranges are a matter of design choice, the important aspect being the ability to provide the particular levels of compression. In that regard, the values of "a" and "b" are selected so that the pressure imposed to patients of various waist size is comparable when the bands are stretched to the specified markings.

TABLE 1

| Band Size | Patient Waist Size | Total Band Length | Number of Strips | a | b | c | d | h |
|---|---|---|---|---|---|---|---|---|
| Small | 24"~28" | 33.5" | 3 | 1.25" | 7" | 2" | 10" | 6" |
| Medium | 29"~34" | 38.5" | 3 | 1.5" | 7.5" | 3.5" | 11" | 7" |
| Large | 35"~41" | 45" | 3 or 4 | 2" | 8" | 4" | 13" | 7.5" |
| Extra Large | 42"~48" | 52" | 3 or 4 | 2.5" | 9" | 6" | 13" | 8.5" |

TABLE 2

| Band Size | Patient Waist Size | Total Band Length | Number of Strips | a | b | c | d | h |
|---|---|---|---|---|---|---|---|---|
| Small | 20"~26" | 30 | 3 | 1.75" | 9" | 3.5" | 12" | 6" |
| Medium | 27"~33" | 37.5" | 3 | 3" | 12" | 3.5" | 13" | 7" |
| Large | 34"~40" | 44.5" | 3 or 4 | 4.5" | 14" | 3.5" | 13" | 7.5" |
| Extra Large | 41"~47" | 51.5" | 3 or 4 | 6" | 16" | 3.5" | 14" | 8" |

The inner or back surface 20"a of the band 20" is illustrated in FIG. 9. This is the surface 20"a that contacts the patient when the band 20" is wrapped about the abdomen or waist of the patient as illustrated in FIG. 1. A trim 22 of suitably stretchable material similar to that illustrated in FIGS. 2 and 3 may be provided around the edges of the band 20".

The front or outer surface 20"b of the band 20" is illustrated in FIG. 9A. The outer surface 20"b is the surface of the band 20" that is exposed when the band is wrapped about the abdomen or waist of a patient as illustrated in FIG. 1. The outer surface 20"b can similarly include areas 24a, 24b such as shown in FIGS. 2A and 3A, that contain either the hooks or loops portion of Velcro® brand hook and loop fasteners. For simplicity, those aspects are not shown in FIG. 9 or 9A, as they would essentially be the same as shown in FIG. 2A or 3A. The band 20" also includes multiple indicator markings 92, 94, 96, 98, which will be described in greater detail below. The band 20" is applied by wrapping it about the abdomen or waist of a patient with the inner surface 20"a in contact with the patient as is shown in FIG. 1. Depending upon the particular implementation, other types of fasteners can be used with, or as an alternative to, the hook and loop fasteners, for example, any bra type clasps or other type of mating fastener capable of holding the strips as intended can be used.

The band 20" also includes narrow, elastic strips. Depending upon the particular implementation of this band 20", the discrete elastic strips can be paired such that there are actually at least three to five individual strips (typically paired and facing opposite directions from the center of the band 20") with one end of each strip having one end that is sewn or otherwise affixed to the outer surface 20"b of the band 20" and an opposing end that is free from the outer surface. Alternatively, the discrete individual strips may be configured with the middle of each affixed to band 20" and both ends of each strip being free ends. As shown in FIGS. 9 and 9A, there are six individual strips, three 25" facing in one direction and the other three 26" facing in the opposite direction.

A fastener 25"a, 26"a, such as either the complementary hooks or loops side of a Velcro® brand hook and loop fastener, is connected to each free end 100 of each of the elastic strips 25", 26" for connection to the two areas 24a, 24b of the band 20" that is illustrated and described for FIGS. 2A and 3A and present in band 20", but omitted from FIG. 9A for simplicity. Each elastic strip 25", 26" is typically approximately between one and two inches wide. In the embodiment illustrated in FIGS. 9 and 9A, the band 20" includes six individual discrete elastic strips 25", 26" with fasteners on each of the free ends 100. The use of at least three elastic strips 25", 26" makes the band 20" more closely conform to the body contour of the patient for more effective compression of internal organs and provides a greater safety margin for the patient not to be overly compressed. It is understood, however, that the number of strips shown in FIG. 9 is exemplary and that the band 20" may incorporate a greater number of strips or, in some variants, a lesser number of elastic strips.

In addition, the band 20" includes multiple indicator markings 92, 94, 96, 98 located successively closer and closer to the ends of the band 20". The indicator markings are placed so as to denote various levels of compression. Depending upon the particular implementation, the indicator markings may be lines, areas that are contrasted in some manner from adjacent areas (for example, by ribbons, color, printed markings or different textures), or even differing materials. The first indicator marking 92, located in this example closest to and on either side of the central portion 102 of the band 20" is a neutral marking that is used to denote an area where the band 20" will be constrained about the abdomen, but will exert substantially no compressive pressure (i.e., less than about 4 mm Hg). Moving in a direction away from the central portion 102 of the band 20", the next indicator marking, on either side of the exterior of the band 20" in this example, is a "LowComp" marking 94, which is used to denote an area where, when the band 20" is about the abdomen of a patient and the strips 25", 26" are affixed in this vicinity, a low compressive pressure will be applied, the pressure generally being in or about equivalent to pressure within the range of about 5 mm Hg to about 12 mm Hg, and nominally centered at a pressure in the range of between about 8 mm Hg and 10 mm Hg, with the ideal being at about 10 mm Hg.

Continuing in a direction away from the central portion 102 of the band 20", the next indicator marking is a "MidComp" marking 96, used to denote an area where affixation of the strips 25", 26" will cause application to the patient of medium compressive pressure, generally in or about equivalent to pressure within the range of about 13 mm Hg to about 22 mm Hg, and nominally centered at a pressure in the range of between about 15 mm Hg to 20 mm Hg, with the ideal being at about 15 mm Hg.

Continuing further in a direction away from the central portion 102 of the band 20", the next indicator marking is a "HiComp" marking 98, which is used to denote the area where the highest or maximum compressive pressure would be applied to the abdomen, at a value generally in or about equivalent to pressure within the range of about 23 mm Hg to about no more than 30 mm Hg, and nominally centered at a pressure in the range of between about 25 mm Hg and 27 mm Hg, with the ideal being at about 25 mm Hg.

Alternatively, depending upon the particular materials used, in some cases, the band 20" may be configured such that, for example, a single size band encompasses two or more of the size bands referred to in Table 1 above. In such a case, because the neutral mark location would be different with each, the band 20" may include multiple sets of indicator markings and/or appropriately marked, length-adjustable, strips 25", 26" so that the proper pressure will be applied when the strips 25", 26" are affixed near the specified marks on different sized patients.

Similarly, the band 20" may be configured with additional or alternative indicator markings denoting different ranges or levels of compression, the particular style or method of denoting the various compression levels being unimportant provided that the LowComp, MidComp and HiComp levels are indicated in some fashion. In addition, in many instances, it may be undesirable to allow imposition of a compressive pressure equivalent to in excess of about 30 mm Hg. Thus, with most single size embodiments, the band 20" will typically not be configured to allow the strips 25", 26" to be affixed to the band in a location much beyond the HiComp indicator marking or where such excessively high compression would be applied.

Advantageously, because narrow strips are used, the patient or the health care personnel should be able to more easily pull each strip to the area of the highest compression force indication marking. In addition, by using a greater number and thinner strips than are conventionally used on simple support belts or vests, better conformation to the waist contour can be achieved so that the compression can be more uniformly applied to the abdominal organs.

As discussed above, the band 20" is first wrapped about the abdomen or waist of a patient to enclose most of the patient's internal abdominal organs. The band 20" is then releasably held in place by stretching the strips 25", 26" so as to bring the free ends of the strips 25", 26" near the indicator marking most appropriate for the desired pressure, the location typically being based upon the specific protocol being followed. The fasteners on the end of the strips 25", 26" are then affixed to the band 20" in the vicinity of the selected indicator marking by releasably engaging the fasteners 25"*a*, 26"*a* with the corresponding fasteners located in the areas 24"*a* and 24"*b* on the outer surface 20"*b* of the band. If the strips 25", 26" are affixed in the area of a particular indicator marking and it is necessary or desired to change the compression to a different level, the free ends of the strips 25", 26" can easily be disengaged by separating the hook and loop portions from each other, moving the strips 25", 26" to the area where the desired new compression level will be applied, and re-engaging the strips to the band 20" at the new location.

Advantageously, through use of multiple strips 25", 26", the instruction for use can advise the user or health care personnel to stretch the strips 25", 26" closest to the edge of the band 20" slightly farther than the strips closest to the middle (from a height "h" perspective) in order to allow the band 20" to better constrain the abdominal organs to be compressed (i.e., so that a lower percentage of the organs will be squeezed out of the area enclosed by the band 20").

Figure 10:
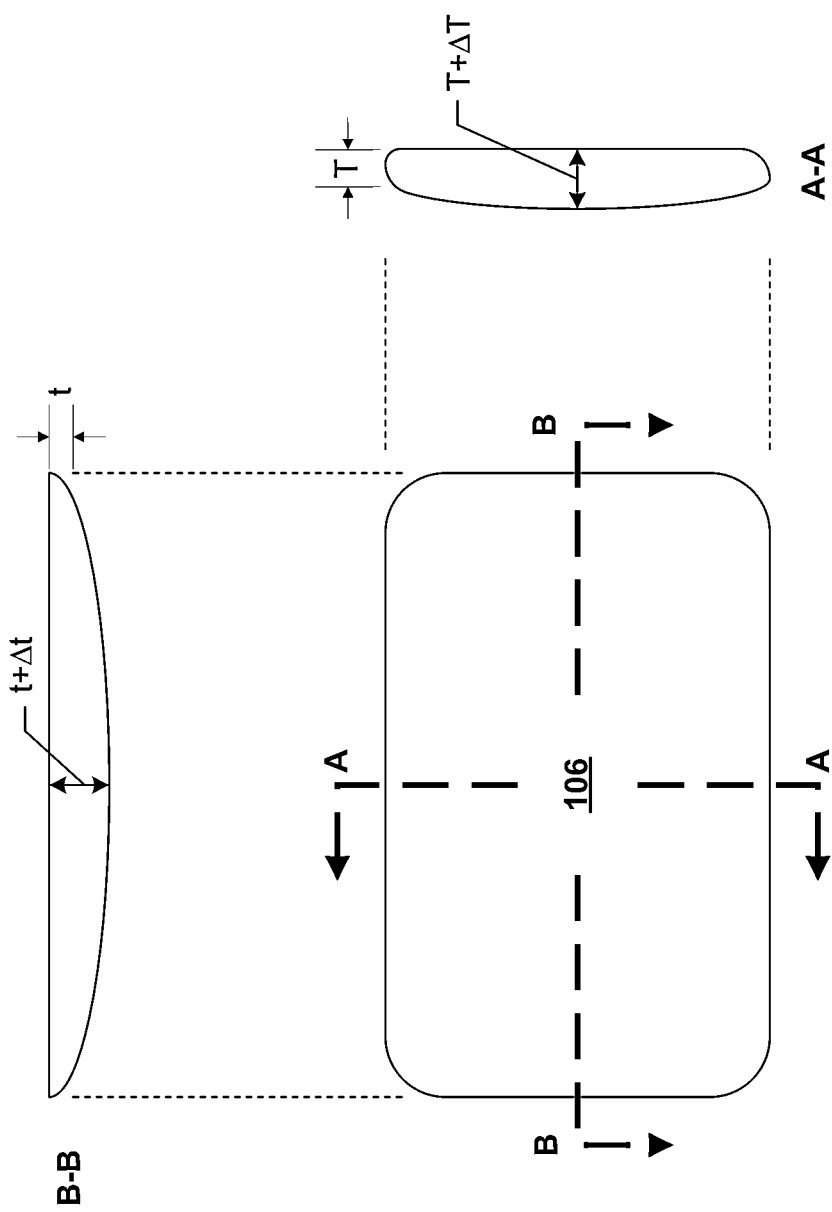
FIG. 10 is a simplified view of an optional pad and its cross section that can be inserted into an optional pocket of the compression vest.

Optionally, the band 20" may also include a pouch or pocket 104 into which a semi-rigid pad 106 may optionally be inserted. The pad 106 will typically be about six inches in height and eight inches in width, and may be contoured to provide for better matching of the contour of the band 20" with the patient's back and, in some cases, also with the back of the chair that the patient is sitting on or the surface the patient may be lying on. Advantageously, a set of multiple pads, having different thicknesses or contour shapes, may be provided so that the most comfortable pad 106 may be selected for insertion into the pouch or pocket 104. In general, consistent with matching the contour of the human lower back, in cross section, the pad 106 will be thicker near the center and thinner towards its edges. This is shown in FIG. 10 in simplified fashion in the end-on cross section of the pad 106 taken along line A-A. Alternatively or additionally, the pad 106 can be contoured in a direction perpendicular to line A-A. This is shown in an example cross section taken at B-B, bearing in mind that any particular pad 106 can be uncontoured, contoured only in the direction shown in the A-A cross section, contoured only in the direction shown in the B-B cross section, or contoured in some fashion in both cross-sectional directions. Note further that the contours shown are each fairly simple for ease of illustration, however, more sophisticated or physiologically accurate back-conforming contours may be used. Note also that, because the pad 106 will add thickness in the center area, at the same stretching of the elastic strips, the waist section around the thicker part of the pad will experience a higher compression pressure. Advantageously, this can provide benefits for patients with orthostatic hypotension (i.e., the development of low blood pressure when standing up from a supine or sitting position) or persons desiring better back support.

Figure 11:
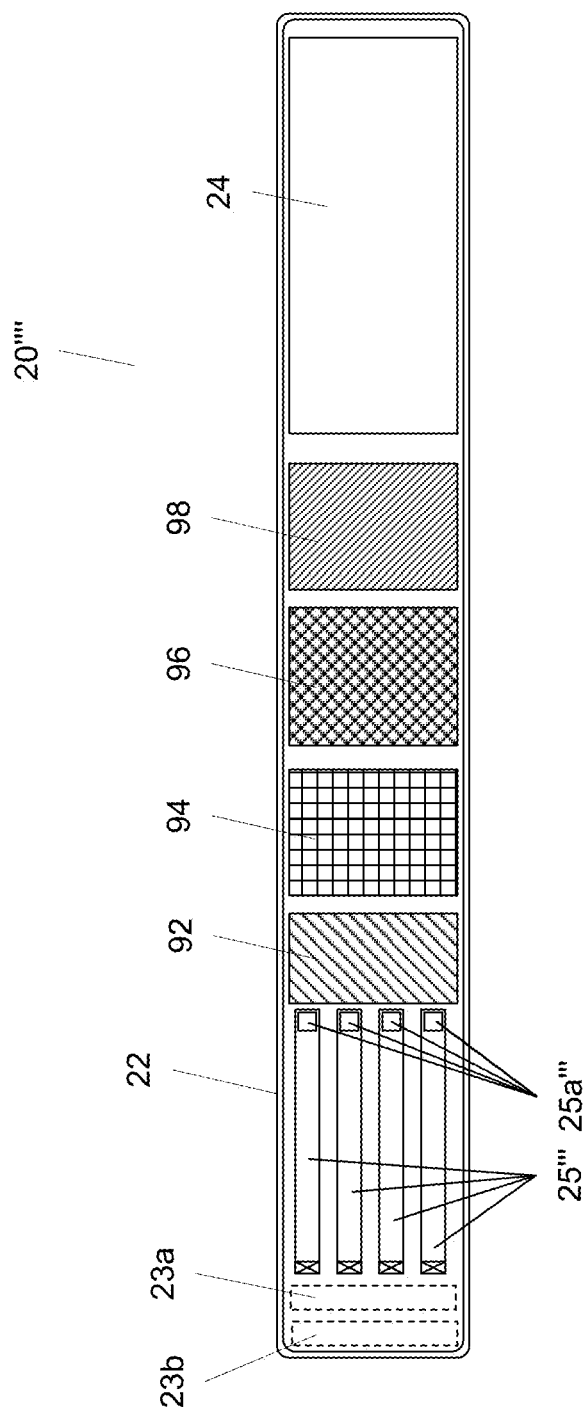
FIG. 11 is a simplified view of yet an additional alternative implementation of a compression vest as described herein.

FIG. 11 illustrates, in simplified form, another alternative non-inflatable variant band 20"" which, as shown, includes two strips of 23*a*, 23*b* of fasteners as in FIGS. 3 and 3A, an area 24 containing complementary fasteners for mating with the fasteners of strips 23*a*, 23*b*, a set of strips 25''' similar to the strips 25" described above that can be used to apply compression pressure of different levels by affixing the fasteners 25"*a* on their free ends to the complementary mating fasteners within the vicinity of the neutral marking 92, the LowComp marking 94, the MidComp marking 96 or the HiComp marking 98, as described above, each of which is indicated using a different color or texture. However, as will be seen with this example implementation, the individual strips 25''' are affixed at the end opposite the free end and only extend in one direction. With this example implementation, the band 20"" compression is applied by wrapping the strips 25''' in only one direction. In all other respects, the example implementation of FIG. 11 is the same as described with respect to the example implementation of FIGS. 10 and 10A.

Alternative Protocols

Depending upon the particular circumstances, in some cases, it may be desirable to use a different protocol to treat a hypotensive patient or vascular complications. This is because, although blood pressure can be an indicator of vascular issues, in many instances blood pressure is not a good indicator on whether there is too much blood volume shifted to the peripheries or the blood volume is too low for proper cardiac filling producing low cardiac output and low blood pressure. Thus, with this protocol one or more additional indicators, changes in blood density, bioimpedance and hematocrit can be used as additional or independent means to set the right compression level.

In accordance with the above-described protocols, the protocols specify that compression pressure is to increase somewhat linearly or stepwise as the treatment progresses while the vest 10 (with band 20, 20' or 20") is being used. The following is an alternative set of protocols that also can be used in conjunction with the vest 10 embodiments described herein to avoid intradialytic hypotension, shock or other vascular complications.

These alternative protocols involve monitoring the bioimpedance of the abdominal organs, the density of blood and/or hematocrit.

For the bioimpedance measurement, four electrodes will be placed horizontally on the patient around the central front portion of the patient's waist. An electric current is then imposed to the two outermost electrodes and the voltage of the two inner electrodes is measured. The bioimpedance is then ascertained in a similar manner to that conventionally used for the bioimpedance measurement of the trunk, or similar to that used for bioimpedance measurements made involving the arm or the calf, such as described in Zhu et al., Extracellular fluid redistribution during hemodialysis: bioimpedance measurement and model, *Physiol Measure*, 29:S491-S501 (2008). Depending upon the particular bioimpedance measurement technique employed, a single frequency and/or multiple frequencies can be used to assess the impedance of the organs in the waist and to quantify the extracellular fluid volume of the tissue and vasculature and the intracellular fluid of the tissue and vasculature.

In addition, or alternatively, blood density and hematocrit will be measured using a conventional blood density or hematocrit monitor or using any other suitable method of determining fluid density, for example, using the monitor described in U.S. Pat. No. 7,220,229, the entirety of which is incorporated herein by reference. For the monitor of U.S. Pat. No. 7,220,229, the venous line of the hemodialysis circuit or a by-pass connecting the radial artery to the radial vein of the patient will be inserted into the slot in the probe of the density monitor so that it can measure the blood density as it would the density of another fluid.

In order to set up for these protocol approaches, in the case of hemodialysis, the patient will have the vest 10 on before the patient is connected to the blood lines for the hemodialysis treatment.

Thereafter, continuous or substantially continuous measurement of bioimpedance, blood density and/or hematocrit begins. Depending upon the particular implementation, bioimpedance alone, blood density alone, hematocrit alone, or a combination of the three may be used. In his regard, for simplicity, the protocols will be described in a manner that allows for either one alone or both and with the various different implementations of vest 10. It should be understood and appreciated however that the capability for both measurements is not required, nor is limitation to a particular one of the vest 10 embodiments described herein. If a measurement capability or a particular aspect of a vest or band is not present in the particular implementation, reference to it should simply be ignored. Thus, reference to X "or" Y relating to a claim herein should be read as only X if there is no Y capability, only Y if there is no X capability, and should include both X and Y only if both X and Y capabilities are present.

With the foregoing in mind, during the course of treatment, compression will be activated with the vest 10 as specified in the protocols below.

If one or more of the following criteria exist:
a) the average blood pressure drops below about 110 mm Hg, and/or
b) the impedance (or primarily the resistance) shows a decrease of less than about 5% of its initial value, and/or
c) the blood density shows an increase by about 1 g/l (and, more preferably, by between about 0.5 g/l to about 0.9 g/l), and/or
d) the hematocrit of blood shows an increase by about 1% (and, more preferably, by between about 0.5% to about 0.9%), then the compression pressure is increased to about 5 mm Hg by, for example, bladder inflation or stretching and affixing the elastic strips of the band at about a lower part of the LowComp marking When treatment is completed, then this compression pressure will be released.

If there is a further measured drop in blood pressure, decrease in impedance, increase in blood density or increase in hematocrit, then further action may be taken based upon, for example, the following additional or alternative protocol.

If the average blood pressure drops below about 100 mm Hg, then the compression pressure may be increased to about 10 mm Hg by, for example, bladder inflation or stretching and affixing the elastic strips of the band to a higher part of the LowComp marking This is referred to as "Course A." Once treatment is complete, then the compression pressure is released.

If, however, before Course A is complete, the impedance shows no decrease from its initial value and/or the blood density shows an increase from its initial value (i.e., before the initiation of Course A) by about 2 g/l (and, more preferably, by between about 1 g/l to about 1.5 g/l) and/or the hematocrit of blood shows an increase from its initial value by about 2% (and, more preferably, by between about 1% to about 1.5%), then the compression pressure may be increased to about 20 mm Hg (and, more preferably, to about 15 mm Hg) by, for example, bladder inflation or stretching and affixing the elastic strips of the band at about the MidComp marking. This is referred to as "Course B." If there is no further change, once treatment is complete, then the compression pressure is released.

However, if, before the completion of Course B, the impedance shows about a 10% increase from its initial value and/or the blood density shows an increase from its initial value by about 3 g/l (and, more preferably, by about 2 g/l, and, ideally between about 1.6 g/l to about 2 g/l) and/or hematocrit shows an increase from its initial value by about 2%, then the compression pressure may be increased to about 25 mm Hg (and, more preferably, to about 20 mm Hg) by, for example, bladder inflation or stretching and affixing the elastic strips of the band to the HiComp marking Again, if there is no further change, once treatment is complete then the compression pressure is released.

The values specified above for density change, bioimpedance change and hematocrit change are only exemplary. It is expected that, in some cases, a physician or other health care professional will further analyze the bioimpedance, density and hematocrit results of a given patient and the patient's quality of life to individualize the values and pressures in the above protocols and they may use different reading values as triggers, higher levels of compression pressure and/or longer treatment time to care for that patient.

Having described and illustrated the principles of this application by reference to one or more preferred embodiments, it should be apparent that the preferred embodiment(s) may be modified in arrangement and detail without departing from the principles disclosed herein and that it is intended that the application be construed as including all such modifications and variations insofar as they come within the spirit and scope of the subject matter disclosed herein.

What is claimed is:

1. A method of treating a hypotensive patient undergoing a treatment, comprising:
   elastically constraining the abdomen of the patient while
   a) concurrently maintaining mobility of the patient's legs and applying non-pulsating compressive pressure to the internal organs within the abdomen of the patient according to a predefined protocol with a compression device about the patient's abdomen, the compression device having at least two discrete elastic strips and at least two markings, each strip having a free end that is selectively, releasably affixable near any one of the at least two markings and each particular marking indicating a different, predetermined compression level from the other markings when the free ends of the strips are releasably affixed near the particular marking, wherein a first of the markings corresponds to a first predetermined compression level that will be applied to the abdomen of the patient when the respective free ends of the elastic strips are affixed to the compressive device near the first of the markings, and a second of the at least two markings corresponds to a second predetermined compression level that will be applied to the abdomen of the patient when the respective free ends of the elastic strips are affixed to the compressive device near the second of the markings, and
   b) infusing a volume of fluid into the patient's bloodstream, such that pooling of blood within the patient's abdominal internal organs and distribution of the infused volume to the abdominal organs are both reduced.

2. The method according to claim 1, further comprising:
   adjusting the compression device from applying the first predetermined compression level to the patient's internal organs within the abdomen to applying the second predetermined compression level to the patient's internal organs within the abdomen in accordance with the predefined protocol.

3. The method according to claim 2, wherein the adjusting comprises moving the respective free ends of the elastic strips from a location near the first of the at least two markings to a location near the second of the at least two markings, and affixing the respective free ends of the elastic strips at the location near the second of the at least two markings.

4. The method according to claim 3, wherein the first predetermined compression level is in the range of about 5 mm Hg to about 12 mm Hg, and the second predetermined compression level is in the range of about 13 mm Hg to about 22 mm Hg.

5. The method according to claim 4, wherein the first predetermined compression level is in the range of about 8 mm Hg to about 10 mm Hg, and the second predetermined compression level is in the range of about 15 mm Hg to about 20 mm Hg.

* * * * *